United States Patent [19]

Cone et al.

[11] Patent Number: 6,046,011
[45] Date of Patent: *Apr. 4, 2000

[54] MAMMALIAN ADRENOCORTICOTROPIC HORMONE RECEPTORS AND USES

[75] Inventors: Roger D. Cone, Oregon City; Kathleen G. Mountjoy, Portland, both of Oreg.

[73] Assignee: Oregon Health Sciences University, Portland, Oreg.

[*] Notice: This patent is subject to a terminal disclaimer.

[21] Appl. No.: 09/105,298

[22] Filed: Jun. 26, 1998

Related U.S. Application Data

[62] Division of application No. 08/478,992, Jun. 7, 1995, Pat. No. 5,773,229, which is a division of application No. 08/077,673, Jun. 15, 1993, Pat. No. 5,554,729, which is a division of application No. 07/866,560, Apr. 10, 1992, Pat. No. 5,280,112.

[51] Int. Cl.$^7$ .................................................. G01N 33/567
[52] U.S. Cl. ........................ 435/7.2; 435/7.21; 435/7.93; 436/503
[58] Field of Search ..................... 435/7.2, 7.21, 435/7.93; 436/503

[56] References Cited

U.S. PATENT DOCUMENTS

| | | | |
|---|---|---|---|
| 4,650,764 | 3/1987 | Temin et al. | 435/350 |
| 4,683,195 | 7/1987 | Mullis | 435/6 |
| 4,683,202 | 7/1987 | Mullis | 436/6 |
| 4,761,371 | 8/1988 | Bell | 435/69.1 |
| 4,861,719 | 8/1989 | Miller | 435/236 |
| 5,280,112 | 1/1994 | Cone et al. | 536/23.5 |
| 5,846,742 | 12/1998 | Lipsky et al. | 436/503 |

OTHER PUBLICATIONS

Hanneman et al., Peptide Hormone as Prohormones, G. Martinez, ed. (Ellis Horwood Ltd.:Chichester, UK) pp 53–82.
DeWied & Jolles, 1982, Physiol. Rev. 62:976–1059.
Oelofsen & Ramachandran, 1983, Arch. Biochem. Biophys. 225: 414–421.
Mertz & Catt, 1991, Proc. Natl. Acad. Sci. USA 88: 8525–8529.
Thomas & Capecchi, 1987, Cell 51: 503–512.
Bertling, 1987, Bioscience Reports 7: 107–112.
Smithies et al., 1985, Nature 317:230–234.
Libert et al., 1989, Science 244:569–72.
Zhou et al., 1990, Nature 347:76–80.
Chirgwin et al., 1979, Biochemistry 18: 5294–5299.
Saiki et al., 1988, Science 239: 487–491.
Sanger et al., 1977, Proc. Natl. Acad. Sci. USA 74:5463–5467.
Probst et al., 1992, DNA & Cell Biol. 11:1–20.
Applebury & Hargrave, 1986, Vision Res. 26:1881–1895.
Dixon et al., 1987, EMBO J. 6:3269–3275.
Karnik et al., 1988, Proc.Natl.Acad. Sci. USA 85:8459–8463.
Spindel et al., 1990, Mol. Endocrinol. 4:1956–1963.
Masu et al., 1987, Nature 329:836–838.
Matsuda et al., 1990, Nature 346:561–564.

*Primary Examiner*—David Saunders
*Attorney, Agent, or Firm*—McDonnell Boehnen Hulbert & Berghoff

[57] ABSTRACT

The present invention relates to a mammalian adrenocorticotropic hormone receptor. The invention is directed toward the isolation, characterization and pharmacological use of mammalian adreocorticotropic hormone receptor, the gene corresponding to this receptor, a recombinant eukaryotic expression construct capable of expressing a mammalian adrenocorticotropic hormone receptor in cultures of transformed eukaryotic cells and such cultures of transformed eukaryotic cells that synthesize mammalian adrenocorticotropic hormone receptor. The invention also provides methods for screening ACTH-R agonists and antagonists in vitro using prerations of receptor from such cultures of eukaryotic cells transformed with a recombinant eukaryotic expression construct comprising the ACTH-R receptor gene. The invention specifically provides human and bovine ACTH-R genes.

14 Claims, 10 Drawing Sheets

```
         10         20         30         40         50         60         70
ACAACACTTT ATATATATTT TTATAAATGT AAGGGGTACA AARGTGCCAT TTTGTTACAT GGATATACCG
         80         90        100        110        120        130        140
TGTAGTGGTG AAGCCTGGGC TTTTAGTGTA TCTGTCATCA GAATAACATA CGTGTTACCC ATAGGAATTT
        150        160        170        180        190        200        210
CTCATCACCC GCCCCCTCCA CCCTTCGAGT CTCCAATGTC CATTCCACAC TCTATATCCA CGTGTATGCA
        220        230        240        250        260        270        280
TATAGCTCCA CATATAAGTG AGAACATGTA GTATTTGACT TCCTCTTTCT GAGTTATTTC ACTTTGATAA
        290        300        310        320        330        340        350
TGGCCTCCAC TTCCATCCAT GTTGCTGCAA AAGACATGAC CTTATTCTTT TTGATAGCTG GGGAGTACTC
        360        370        380        390        400        410        420
CATTGTGTAT ATGTACCACA TTTNCTTTAT CCATTCACCC ATTGANGAAC ACTTAGTTGA TTCCATATCT
        430        440        450        460        470        480        490
TTGCTATTGT CACTAGTGCT GCAATAAACA TACATGTGCA GGCTCCTTCT AATATACTGA TTTATATTTT
        500        510        520        530        540        550        560
ATGGAGAGAG ATAGAGTTCT TAGCGAGTGT GCTGTTTATT TCTAGTGTAC TTGCAACTAA TATTCTGTAT
        570        580        590        600        610        620        630
ACTCCCTTTA GGTGATTGGA GATTTAACTT AGATCTCCAG CAAGTGCTAC AAGAAGAAAA GATCCTGAAG
        640        650        660        670        680        690        700
AATCAATCAA GTTTCCGTGA AGTCAAGTCC AAGTAACATC CCCGCCTTAA CCACAAGCAG GAGAAATGAA
        710        720        730        740        750        760        770
GCACATTATC AACTCGTATG AAAACATCAA CAACACAGCA AGAAATAATT CCGACTGTCC TCGTGTGGTT
```

Figure 1A

```
780              790              800              810              820              830              840
TTGCCGGAGG  AGATATTTTT  CACAATTTCC  ATTGTTGGAG  TTTTGGAGAA  TCTGATCGTC  CTGCTGGCTG
850              860              870              880              890              900              910
TGTTCAAGAA  TAAGAATCTC  CAGGCACCCA  TGTACTTTTT  CATCTGTAGC  TTGGCCATAT  CTGATATGCT
920              930              940              950              960              970              980
GGGCAGCCTA  TATAAGATCT  TGGAAAATAT  CCTGATCATA  TTGAGAAACA  TGGGCTATCT  CAAGCCACGT
990              1000             1010             1020             1030             1040             1050
GGCAGTTTTG  AAACCACAGC  CGATGACATC  ATCGACTCCC  TGTTTGTCCT  CTCCCTGCTT  GGCTCCATCT
1060             1070             1080             1090             1100             1110             1120
TCAGCCTGTC  TGTGATTGCT  GCGGACCGCT  ACATCACCAT  CTTCCACGCA  CTGCGGTACC  ACAGCATCGT
1130             1140             1150             1160             1170             1180             1190
GACCATGCGC  CGCACTGTGG  TGGTGCTTAC  GGTCATCTGG  ACGTTCTGCA  CGGGGACTGG  CATCACCATG
1200             1210             1220             1230             1240             1250             1260
GTGATCTTCT  CCCATCATGT  GCCCACAGTG  ATCACCTTCA  CGTCGCTGTT  CCCGCTGATG  CTGGTCTTCA
1270             1280             1290             1300             1310             1320             1330
TCCTGTGCCT  CTATGTGCAC  ATGTTCCTGC  TGGCTCGATC  CCACACCAGG  AAGATCTCCA  CCCTCCCCAG
1340             1350             1360             1370             1380             1390             1400
AGCCAACATG  AAAGGGGCCA  TCACACTGAC  CATCCTGCTC  GGGGTCTTCA  TCTTCTGCTG  GGCCCCTTT
1410             1420             1430             1440             1450             1460             1470
GTGCTTCATG  TCCTCTTGAT  GACATTCTGC  CCAAGTAACC  CCTACTGCGC  CTGCTACATG  TCTCTCTTCC
```

Figure 1B

```
      1480            1490            1500            1510            1520            1530            1540
AGGTGAACGG      CATGTTGATC      ATGTGCAATG      CCGTCATTGA      CCCCTTCATA      TATGCCTTCC      GGAGCCCAGA 1550            1560            1570            1580            1590            1600            1610
GCTCAGGGAC      GCATTCAAAA      AGATGATCTT      CTGCAGCAGG      TACTGGTAGA      ATGGCTGATC      CCTGGTTTTA 1620            1630            1640            1650            1660            1670            1680
GAATCCATGG      GAATAACGTT      GCCAAGTGCC      AGAATAGTGT      AACATTCCAA      CAAATGCCAG      TGCTCCTCAC 1690            1700            1710            1720            1730            1740            1750
TGGCCTTCCT      TCCCTAATGG      ATGCAAGGAT      GACCCACCAG      CTAGTGTTTC      TGAATACTAT      GGCCAGGAAC 1760            1770            1780            1790            1800            1810            1820
AGTCTATTGT      AGGGGCAACT      CTATTTGTGA      CTGGACAGAT      AAAACGTGTA      GTAAAAGAAG      GATAGAATAC 1830            1840            1850            1860            1870            1880            1890
AAAGTATTAG      GTACAAAAGT      AATTANGGTT      TNNGCNATTA      CTTNNMATGA      CNNNAAATNG      CANTTACTTT 1900            1910            1920            1930            1940            1950            1960
TGCACCAATC      TAGTAAAACA      GCAATAAAAA      TTCAAGGGCT      TTGGGCTAAG      GCAAAGACTT      GCTTTCCTGT 1970            1980            1990            2000            2010            2020
GGACATSTAA      CAAGCCAGTT      CTGANGGCGG      CCTTTCCAGG      TGGAGGCCAT      TGCAGCCAAT      TTCAGAGT
```

Figure 1C

```
  10         20         30         40         50         60         70
GGGGCCAGAA AGTTCCTGCT TCAGAGCAGA AGATCTTCAG CAAGAACTAC AAAGAAGAAA AGATTCTGGA
  80         90        100        110        120        130        140
GAATCAATCA AGTTCCTGT CAAGTTCCAG TAACGTTTCT GTCTTAACTG CACACAGGAA AGATGAAACA
 150        160        170        180        190        200        210
CATTCTCAAT CTGTATGAAA ACATCAACAG TACAGCAAGA AATAACTCAG ACTGTCCTGC TGTGATTTTG
 220        230        240        250        260        270        280
CCAGAGAGA TATTTTTCAC AGTATCCATT GTTGGGGTTT TGGAGAACCT GATGGTCCTT CTGGCTGTGG
 290        300        310        320        330        340        350
CCAAGAATAA GAGTCTTCAG TCGCCCATGT ACTTTTTCAT CTGCAGCTTG GCTATTTCCG ATATGCTGGG
 360        370        380        390        400        410        420
GAGCCTGTAC AAGATTTTGG AAAACGTTCT GATCATGTTC AAAAACATGG GTTACCTCGA GCCTCGAGGC
 430        440        450        460        470        480        490
AGTTTTGAAA AGCACAGCAG ATGATGTGGT GGACTCCCTG TTCATCCTCT CCCTTCTCGG CTCCATCTGC
 500        510        520        530        540        550        560
AGCCTGTCTG TGATTGGGCT GACCGGTCAT CACAATCTTC CACGCTCTGC AGTACCACCG CATCATGACC
 570        580        590        600        610        620        630
CCGCACCGTG CCCTCGTCAT CTGACGGGTCC TCTGGGCAGG CTGCACAGGC CTGTTCCCGC AGTGGCATTA CCATCGTGAC
 640        650        660        670        680        690        700
CTTCTCCCAT CACGTCCCCA CAGTGATGCG CTTCACAGCG CTGTTCCCGC TGATGCTGGC CTTCATCCTG
 710        720        730        740        750        760        770
TGCCTCTACG TGCACATGTT CCTGCTGGCC CGCTCCCACA CCAGGAGGAC CCCCTCCCTT CCCAAAGCCA
```

```
780                790                800                810                820                830                840
ACATGAGAGG         GGCCGTCACA         CTGACTGTCC         TGCTCGGGGT         CTTCATTTTC         TGTTGGGCAC         CCTTTGTCCT
850                860                870                880                890                900                910
TCATGTCCTC         TTGATGACAT         TCTGCCCAGC         TGACCCCTAG         TGTGCCTGCT         ACATGTCCCT         CTTCCAGGTG
920                930                940                950                960                970                980
AATGGTGTGT         TGATCATGTG         TAATGCCATC         ATCGACCCCT         TCATATATGC         CTTCGGAGCC         CAGAGCTCAG
990                1000               1010               1020               1030               1040               1050
GGTCGGCATTC        AAAAAGATGG         TTTATCTGCA         ACTGTTACCA         GTAGAATGAT         TGGTCCCTGA         TTTTAGGAGC
1060               1070               1080               1090               1100
CACAGGGATA         TACTGTCAGG         GACAGAGTAG         CGTGACAGAC         CAACAACACT         AGGACT
```

Figure 3A

```
mouse MSH-R                                                           mstQepQksLvGSLNSnaTsh--  21
                                                                          ||||| ||||||  ||
human MSH-R                                                           mavQgsQrrLlGSLNStpTaipq  23
human ACTH-R                                                                    mkhiinsye      9
rat cannab.                                                      m-(101)-----------------    102

I                                   II
mouse MSH-R    LGLATNQsepwCLyVSIPDGLFLSLGLVSLVENvLVViAItKNRNLHcPMYyFICCLALSD   82
               ||||||| |  || ||| ||||||||||||||| || |  ||||||| |||||| |||||||
human MSH-R    LGLAaNQtgarCLeVSIsDGLFLSLGLVSLVENaLVVatIaKNRNLHsPMYcFICCLALSD   84
                  |    |  |        |   |        |  |  |  |   ||   |   || |
human ACTH-R   ninnTarnnsdCprVvlPeeifFTisiVgvlENlivllAvfKNkNLqaPMYfFICsLAiSD   70
                                    :   :       :   :    :          :
rat cannab.    --------------------L-LTLG---VLENLLVL--I---R-L--P-Y-FI-SLA--D  163

III
mouse MSH-R    LmVSvsiVLETtiILLLEvGiLVARvAlvQQLDNlIDVliCgSMvSSLCFLGiIAiDRYIS   143
                | || | |||  |||||||| ||| | |  ||||||||| |||| |||||| || |||||
human MSH-R    LLVSgtnVLETavILLLEaGaLVARaAv1QQLDNvIDVitCsSMLSSLCFLGaIAvDRYIS   145
                || |   |||   || |  |   |  :    ||| ||| :  | : ||| |   ||||
human ACTH-R   mLgSlykilEnilIiLrnmGyLkpRgsfettaDdiIDslfv1SlIgSifsLsvIAaDRYIt   131
                ||| |                 |                  |         |||||
rat cannab.    LLGSV--V---------------P-----------------V----GSLF-L---AIDRYIS   224
```

Figure 3B

```
                    IV                                                              V
mouse MSH-R   IFYALRYHSIVTLPRArRAVvgIWmvSivsSTLFItyYkHtAVLLCLvtFFLAMLaIMAiL    204
HUMAN MSH-R   IFYALRYHSIVTLPRApRAVaaIWvaSvVfSTLFIaYYdHVAVLLCLvvPFFLAMLVLMAvL    206
human ACTH-R  IFhALRYHSIVTmrRtvvvltvIWTfctgtgitmvifshHVptvitftslFplMLVfilcL     192
rat cannab.   I---L-Y--IVT-P-AVVA----WT-IV--L-----------------------FPL----L-- 285
                                                                      VI
mouse MSH-R   YaHMFtRACQHvQGIAqLHKRQRsirQGFsLKGAaTLTILLGIFFLCWGPFFLHLLLIVLC    264
human MSH-R   YVHMLaRACQHaQGIARLHKRQRpvhQGFgLKGAvTLTILLGIFFLCWGPFFLHLtLIVLC    266
human ACTH-R  YVHMF---------lIARsHtRkistlpranmKGAiTLTILLGvFifCWaPFvLHvLLmtfC    245
rat cannab.   --------(31)----RP----R-----A-TL---L-V-I-CWGP-------------      373
                                                 VII
mouse MSH-R   PqHPTCsCIFKNfPNLFLLLIvlsstvDPLIYAFRSQELRmTLKEVLlCS--W             317
human MSH-R   PeHPTCgCIFKNfPNLFLaLIiCNAiIDPLIYAFhSQELRrTLKeVLtCS--W             316
human ACTH-R  PsnPyCaCymslFqvngMLImCNAvIDPfIYAFRSpKLRdafKkmifCSryW              297
rat cannab.   -------F----ML--LNSTV-P-IYA-RS--LR-AF--M-F-S---(56)              483
```

MAMMALIAN ADRENOCORTICOTROPIC HORMONE RECEPTORS AND USES

This application is a divisional of U.S. Ser. No. 08/478,992, filed Jun. 7, 1995 now U.S. Pat. No. 5,773,229, issued Jun. 30, 1998, which is a divisional of U.S. Ser. No. 08/077,673, filed Jun. 15, 1993, now U.S. Pat. No. 5,554,729, issued Sep. 10, 1996, which is a divisional of U.S. Ser. No. 07/866,560, filed Apr. 10, 1992, now U.S. Pat. No. 5,280,112, issued Jan. 18, 1994. The disclosures of each of these prior applications are considered as being part of the disclosure of the application and are explicitly incorporated by reference herein.

This invention was made with government support under 1R01DK41921-03, 1R01DK43859-01, and 1P01DK44239-10A1 by the National Institutes of Health. The government has certain rights in the invention.

BACKGROUND OF THE INVENTION

1. Field of the Invention

This invention relates to adrenocorticotropic hormone receptors from mammalian species and the genes corresponding to such receptors. Specifically, the invention relates to the isolation, cloning and sequencing of a human adrenocorticotropic hormone receptor gene. The invention also relates to the isolation, cloning and sequencing of a bovine adrenocorticotropic hormone receptor gene. The invention relates to the construction of eukaryotic recombinant expression constructs capable of expressing these adrenocorticotropic hormone receptors in cultures of transformed eukaryotic cells, and the production of the adrenocorticotropic hormone receptor in such cultures. The invention relates to the use of such cultures of transformed eukaryotic cells to produce homogeneous compositions of such adrenocorticotropic hormone receptors. The invention also provides culture of such cells producing adrenocorticotropic hormone receptor for the characterization of novel and useful drugs.

2. Background of the Invention

The proopiomelanocortin (POMC) gene product is processed to produce a large number of biologically active peptides. Two of these peptides, alpha-melanocyte stimulating hormone (αMSH), and adrenocorticotropic hormone (ACTH) have well under roles in control of melanocyte and adrenocortical function, respectively. Both of these hormones, however, are found in a variety of forms with unknown functions. The melanocortin peptides also have a diverse array of biological activities in other tissues, including the brain, and immune system, and bind to specific receptors there with a distinct pharmacology (see, Hanneman et at., in *Pepde Hormone* as *Prohowmonces*, G. Mar , ed. (Ellis Horwood Ltd.: Chichester, UK) pp. 53–82; DeWied & Jolles, 1982, Physiol. Rev. 62: 976–1059 for reviews).

A complete understanding of these peptides and their diverse biological activities requires the isolation and characterization of their corresponding receptors. Some biochemical studies have been reported in the prior art.

Oelofsen & Ramachandran, 1983, Arch. Biochem. Biophys. 225: 414–421 disclose receptor binding studies on ACTH receptors on rat adipocytes.

Mertz & Catt, 1991, Proc. Natl. Acad. Sci. USA 88: 8525–8529 disclose functional expression of ACTH receptors in *Xenopus laevis* oocytes following injecton of total cellular RNA from adrenal tissue.

Moore et al., 1991, Endocrinology 34: 107–114 relates to Allgrove syndrome, an autosomal recessive syndrome characterized by ACTH insensitivity.

The present invention comprises a human adrenocorticotropic hormone receptor gene, the nucleotide sequence of this gene and the deduced amino acid sequence of its cognate protein, a homogeneous composition of the adrenocorticotropic hormone receptor, nucleic acid hybridization probes and a method for determining the tissue distribution of expression of the gene, a recombinant expression construct capable of expressing the gene in cultures of transformed eukaryotic cells, and such cultures of transformed eukaryotic cells useful in the characterization of novel and useful drugs. The present invention also comprises the bovine adrenocorticotropic hormone receptor gene.

SUMMARY OF THE INVENTION

The present invention relates to the cloning, expression and functional characterization of mammalian adrenocorticotopc hormone receptor (ACTH-R) genes. The invention comprises the nucleotide sequence of these genes encoding the mammalian ACTH-Rs and the deduced amino acid sequences of the cognate proteins, as well as tissue distribution patterns of expression of these genes.

In particular, the present invention is directed toward the isolation, characterization and pharmacological use of the human ACTH-R, the gene corresponding to this receptor, a nucleic acid hybridization probe comprising DNA sequences of the human ACTH-R a recombinant eukaryotic expression construct capable of expressing the human ACTH-R in cultures of transformed eukaryotic cells and such cultures of transformed eukaryotic cells that synthesize the human ACTH-R, a homogeneous composition of the human ACTH-R, and antibodies against and epitopes of the human ACTH-R.

The present invention is also directed toward the isolation, characterization and pharmacological use of the bovine ACTH-R, the gene corresponding to this receptor, a nucleic acid hybridization probe comprising DNA sequences of the bovine ACTH-R, a recombinant eukaryotic expression construct capable of expressing the bovine ACTH-R in cultures of transformed eukaryotic cells and such cultures of transformed eukaryotic cells that synthesize the bovine ACTH-R, a homogeneous composition of the bovine ACTH-R, and antibodies against and epitopes of the bovine ACTH-R.

It is an object of the invention to provide a nucleotide sequence encoding a mammalian ACTH-R. In a preferred embodiment of the invention, the nucleotide sequence encodes the human ACTH-R. In another prefer embodiment, the nucleotide sequence encodes the bovine The present invention includes a nucleotide sequence encoding a human ACTH-R receptor derived from a DNA molecule isolated from a human genomic library (SEQ ID NO:5). In this embodiment of the invention, the nucleotide sequence includes 2028 nucleotides of the human ACTH-R gene comprising 893 nucleotides of coding sequence, 696 nucleotides of 5' untranslated sequence and 439 nucleotides of 3' untranslated sequence.

The present invention also includes a nucleotide sequence encoding a bovine ACTH-R derived from a cDNA molecule isolated from a cDNA library constructed with bovine RNA (SEQ ID NO:3). In this embodiment of the invention, the nucleotide sequence includes 1106 nucleides of the bovine ACTH-R gene comprising 893 nucleotides of coding sequence, 133 nucleotides of 5' untranslated sequence and 82 nucleotides of 3' untranslated sequence.

The invention includes nucleoide sequences of mammalian ACTH-Rs, most preferably bovine and human ACTH-R (SEQ ID NOs:3&5), and includes allelic variations of these nucleotide sequences and the corresponding ACTH-R molecule, either naturally occuring or the product of in vitro chemical or genetic modification, each such variant having essentially the same nucleotide sequence as the nucleode sequence of the correspding ACTH-R disclosed herein, wherein the resulting ACTH-R molecule has substantially the same biological properties as the ACTH-R molecule corresponding to the nucleotide sequence described herein. The term "substantially homologous to " as used in this invention encompasses such allelic variability as described in this paragraph.

The invention also includes a predicted amino acid sequence for the bovine (SEQ ID NO:4) and human (SEQ ID NO:6) ACTH-R deduced from the nucleotide sequence comprising the complete coding sequence of the bovine (SEQ ID NO:3) and human (SEQ ID NO:5) ACTH-R gene as described herein.

In another aspect the invention comprises a homogeneous composition of a 34 kiodalton bovine ACTH-R or derivative thereof, wherein the amino acid sequence of the ACTH-R or derivative thereof comprises a sequence shown in FIG. 3 (SEQ ID NO:4).

In another aspect, the invention comprises a homogeneous composition of a 34 kilodalton human ACTH-R or derivative thereof, wherein the amino acid sequence of the ACTH-R or derivative thereof comprises a sequence shown in FIG. 3 (SEQ ID NO:6).

This invention provides both nucleotide and amino acid probes derived from thes sequences. The invention includes probes isolated from either cDNA or genomic DNA clones, as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide sequences of mammal ACTH-R, preferably the bovine or human ACTH-R, for use as nucleic acid hybridization probes to determine the pattern, amount and extent of expression of this retor in various tissues of mammals, including humans. It is also an object of the present invention to provide nucleic acid hybridization probes derived from the sequences of the bovine or human ACTH-R to be used for the detection and diagnosis of genetic diseases. It is an object of this invention to provide nucleic acid hybridization probes derived from the DNA sequences of the bovine or human ACHT-R to be used for the detection of novel related receptor genes.

The present invention also includes synthetic peptides made using the nucleotide sequence information comprising cDNA or genomic clone embodiments of the invention. The invention includes either naturally occurring or synthetic peptides which may be used as antigens for the production of ACTH-R specific antibodies, or used for competitors of the ACTH-R molecule for drug binding, or to be used for the production of inhibitors of the binding of agonists or antagonists or analogues thereof to ACTH-R molecule.

The present invention also provides antibodies against and epitopes of mammalian ACTH-Rs, preferably bovine or human ACTH-R proteins. It is an object of the present invention to provide antibodies that is immunologically reactive to a mammalian ACTH-R protein. It is a particular object of the invention to provide a monoclonal antibodies to mammalian ACTH-R protein, most preferably bovine or human ACTH-R protein.

It is also an object of the present invention to provide a hybridoma cell line that produces such an antibody. It is a particular object of the invention to provide a hybridoma cell line that is the result of fusion between a non-immunoglobulin producing bovine myeloma cell line and spleen cells derived from an animal immunized with a human cell line which expresses ACTH-R antigen. The present invention also provides a hybridoma cell line that produces such an antibody, and that can be injected into a living animal to provide an ascites fluid from the bovine that is comprised of such an antibody.

The present invention also provides a pharmaceutical composition comprising a therapeutically effective amount of a monoclonal antibody that is immunologically reactive to a mammalian ACTH-R, preferably a bovine or human ACTH-R, and in a pharmaceutically acceptable carrier.

It is a further object of the present invention to provide an epitope of a mammalian ACTH-R protein wherein the epitope is immunologically reactive to an antibody specific for the mammalian ACTH-R. In preferred embodiments, the epitope is derived from bovine or human ACTH-R protein.

It is another Object of the invention to provide a chimeric antibody that is immunologically reactive to a mammalian ACTH-R protein. In a preferred embodiment, the chimeric antibody is a monoclonal antibody. In a preferred embodiment, the ACTH-R is a bovine or human ACTH-R.

The present invention provides a recombinant expression construct comprising the nucleotide sequence of a mammalian ACTH-R, preferably the bovine or human ACTH-R and sequences sufficient to direct the synthesis of bovine or human ACTH-R in cultures of transformed eukaryotic cells. In a preferred embodiment, the recombinant expression construct is comprised of plasmid sequences derived from the plasmid pcDNAI/neo and cDNA or genomic DNA of bovine or human ACTH-R gene. This invention includes a recombinant expression construct comprising essentially the nucleotide sequences of genomic or cDNA clones of bovine or human ACTH-R in an embodiment that provides for their expression in cultures of transformed eukaryotic cells.

It is also an object of this invention to provide cultures of transformed eukaryotic cells that have been transformed with such a recombinant expression construct and that synthesize mammalian, preferably bovine or human, ACTH-R protein. In a preferred embodiment, the invention provides human 293 cells that synthesize bovine ACTH-R. In an additional preferred embodiment, the invention provides human 293 cells that synthesize human ACTH-R protein.

The present invention also includes protein preparation of mammalian, preferably bovine or human ACTH-RH, and preparations of membranes containing mammalian ACTH-R, derived from cultures of transformed eukaryotic cells. In a preferred embodiment, cell membranes containing bovine ACTH-R protein are isolated from 293 cell cultures transformed with a recombinant expression construct that dire the synthesis of bovine ACTH-R. In another preferred embodiment, cell membranes containing human ACTH-R protein are isolated from 293 cell cultures transformed with a recombinant expression construct that directs the synthesis of human ACTH-R.

It also an object of this invention to provide mammalian, preferably bovine or human ACTH-R for use in the in vitro screening of novel adenosine agonist and antagonist compounds. In a preferred embodiment, membrane portions containing the bovine ACTH-R, derived from cultures of transformed eukaryotic cells, are used to determine the drug dissociation properties of various novel adenosine agonist and antagonist compounds in vitro. In another preferred embodiment, membrane portions containing the human ACTH-R, derived from cultures of transformed eukaryotic cells, are used to determine the drug dissociation properties of various novel adenosine agonist and antagonist compounds in vitro. These properties are then used to characterize such novel compounds by comparison to the binding properties of known bovine or human ACTH-R agonists and antagonists.

The present invention is also useful for the in vivo detection of analogues of agonists or antagonists of ACTH-R, known or unknown, either naturally occurring or as the embodiments of a drug.

It is an object of the present invention to provide a method for the quantitative detection of agonists or antagonists, or analogues thereof, of ACTH-R, known or unknown, either naturally occurring or as the embodiments of a drug. It is an additional object of the invention to provide a method to detect such agonists, antagonists, or analogues thereof in blood, saliva, semen, cerebrospinal fluid, plasma, lymph, or any other bodily fluid.

Specific preferred embodiments of the present invention will become evident from the following more detailed description of certain preferred embodiments and the claims.

DESCRIPTION OF THE DRAWINGS

The file of this patent contains at least one drawing executed in color. Copies of this patent with color drawing (s) will be provided by the Patent and Trademark Office upon request and the payment of the necessary fee.

FIGS. 1A through 1C illustrates the nucleotide sequence of the human (SEQ ID NO:3) adrenocorticotropic hormone receptor.

FIGS. 2A–2B illustrates the nucleotide sequence of the bovine (SEQ ID NO:5) adrenocorticotropic hormone receptor.

FIGS. 3A–3B presents an amino acid sequence comparison between the human adrenocorticotropic hormone receptor protein and the mouse and human melanocyte stimulating hormone receptor proteins.

DETAILED DESCRIPTION OF THE PREFERRED EMBODIMENTS

Figure 4:
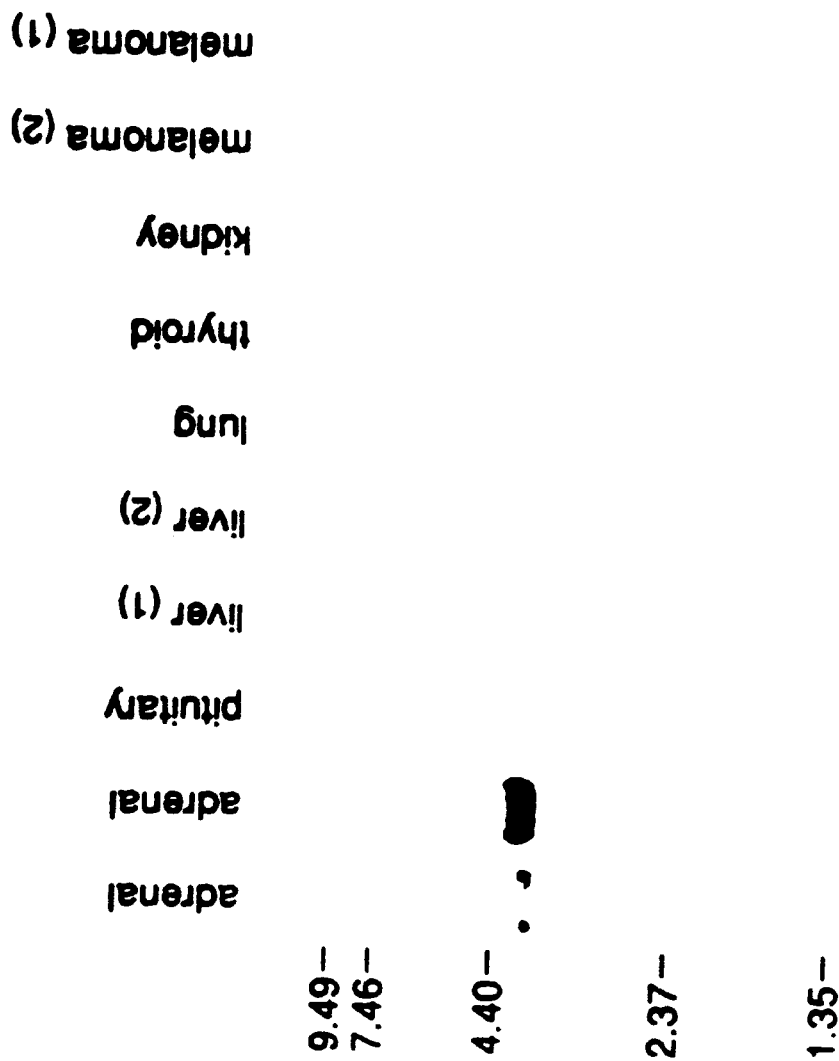
FIG. 4 illustrate the tissue distribution of human adrenocorticotropic hormone receptor gene expression by Northern blot hybridization.

The term "adrenocorticotropic hormone receptor" as used herein refers to proteins substantially homologous to, and having substantially the same biological activity as, the protein coded for by the nucleotide sequence depicted in FIGS. 1A and 1B (SEQ ID NO.: 3) and FIGS. 2A and 2B (SEQ ID No.: 5). This definition is intended to encompass natural allelic variations in the adrenocorticotropic hormone receptor sequence. Cloned genes of the present invention may code for ACTH-Rs of any species of origin, including, for example, bovine, rat, rabbit, cat, and human, but preferably code for receptors of mammalian, most preferably bovine and human, origin.

Nucleic acid hybridization probes provided by the invention comprise DNA sequences that are substantially homologous to the DNA sequences in FIGS. 1A and 1B (SEQ ID NO.:3) and FIGS. 2A and 2B (SEQ ID No.: 5). Nucleic acid probes are useful for detecting ACTH-R gene expression in cells and tissues using techniques well-known in the art, including but not limited to Northern blot hybridization, in situ hybridization and Southern hybridization to reverse transcriptase polymerase chain reaction product DNAs. The probes provided by the present invention, including oligonucleotide probes derived therefrom, are useful are also useful for Southern hybridization of mammalian, preferably human, genomic DNA for screening for restriction fragment length polymorphism (RFLP) associated with certain genetic disorders.

The production of proteins such as the ACTH-R from cloned genes by genetic engineering is well known. See, e.g., U.S. Pat. No. 4,761,371 to Bell et al. at Col. 6 line 3 to Col. 9 line 65. (The disclosure of all U.S. patent references cited herein is to be incorporated herein by reference.) The discussion which follows is accordingly intended as an overview of this field, and is not intended to reflect the full state of the art.

DNA which encodes the ACTH-R may be obtain, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the ACTH-R gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, ACTH-R gene sequences may be obtained by use of the polymerase chain reaction (PCR) procedure, with the PCR oligonucleotide primers being produced from the ACTH-R gene sequence provided herein. See U.S. Pat. Nos. 4,683,195 to Mullis et al. and 4,683,202 to Mullis.

The ACTH-R may be synthesized in host cells transformed with a recombinant expression construct comprising a DNA sequence encoding the ACTH-R. Such a recombinant expression construct can also be comprised of a vector that is a replicable DNA construct. Vectors are used herein either to amplify DNA encoding the ACTH-R and/or to express DNA which encodes the ACTH-R. For the purposes of this invention, a recombinant expression construct is a replicable DNA construct in which a DNA sequence encoding the ACTH-R is operably linked to suitable control sequences capable of effecting the expression of the ACTH-R in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vecors will contain replicon and control swat which arm derived from species compatible with the intended expression host A preferred vector is the plasmid pcDNAI/neo. Transformed host cells are cells which have been transformed or transfected with recombinant expression constructs made using recombinant DNA techniques and comprising a mammalian ACTH-R. Transformed host cells may ordinarily express the mammalian ACTH-R, but host cells transformed for purposes of cloning or amplifying nucleic acid hybridization probe DNA need not express the receptor. When expressed, the mammalian ACTH-R will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in the same translational reading frame.

Cultures of cells derived from multicellular organisms are a desirable host for recombinant ACTH-R synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, and WI138, BHK, COS-7, CV, and MDCK cell lines. Human 293 cells are preferred. Expression vectors for such cells ordinarily include (if necessary) an origin of replication, a promoter located upstream from the gene to be expresed, along with a ribosome binding site, RNA splice sites (if intron-containing genomic DNA is used), a polyadenylation site, and a transcriptional termination sequence.

An origin of replication may be provided either by construction of the vector to include an exogenous origin, such as may be derived from SV40 or other viral source (e.g., polyoma, adenovirus, VSV, or MPV), or may be provided by the host cell chromosomal replication mechanism. If the vector is integrated into the host cell chromosome, the latter may be sufficient.

The invention provides homogene compositions of mammalian ACTH-R protein produced by transformed eukaryotic cells a provided herein. Such homogeneous compositions are intended to be comprised of mammalian ACTH-R protein that comprises 90% of the protein in such homogeneous composition.

Mammalian ACTH-R protein made from cloned genes in accordance with the present invention may be used for screening agonist compounds for ACTH-R activity, or for determining the amount of a ACTH-R agonist or antagonist drug in a solution (e.g., blood plasma or serum). For example, host cells may be transformed with a recombinant expression construct of the present invention, ACTH-R expressed in that host, the cells lysed, and the membranes from those cells used to screen compounds for ACTH-R binding activity. Competitive binding assays in which such procedures may be carried out are well known in the art By selection of host cells which do not ordinarily express ACTH-Rs, pure preparations of membranes containing ACTH-Rs can be obtained. Further, ACTH-R agonists and antagonists can be identified by transforming host cells with vectors of the present invention. Membranes obtained from such cells can be used in binding studies wherein the drug dissociation activity is monitored.

The recombinant expression constructs of the present invention are useful in molecular biology to transform cells which do not ordinarily express the ACTH-R to thereafter express this receptor. Such cells are useful as intermediates for making cell membrane preparations useful for receptor binding assays, which are in turn useful for drug screening. Further, genes and vectors comprising the recombinant expression construct of the present invention are useful in gene therapy. For such purposes, retroviral vectors as described in U.S. Pat. No. 4,650,764 to Temin & Watanabe or U.S. Pat. No. 4,861,719 to Miller may be employed. Cloned genes of the present invention, or fragments thereof, may also be used in gene therapy carried out homologous recombination or sitedirected mutagenesis. See general Thomas & Capecchi, 1987, Cell 51: 503–512; Bertling, 1987, Bioscience Reports 7: 107–112; Smithies et at., 1985, Nature 312: 230–234.

Oligonucleotides of the present invention are useful as diagnostic tools for probing ACTH-receptor gene expression in tissues. For example, tissues can be probed in situ with oligonucleotide probes carrying detectable groups by conventional autoradiography techniques, as explained in greater detail in the Examples below, to investigate native expression of this receptor or pathological conditions relating thereto Further, chromosomes can be probed to investigate the presence or absence of the ACTH-R gene, and potential pathological conditions related thereto, as also illustrated by the Examples below.

The invention also provides antibodies that are immunologically reactive to a mammalian ACTH-R. The antibodies provided by the invention can be raised in animals by inoculation with cells that express a mammalian ACTH-R or epitopes of a mammalian ACTH-R using methods well known in the art. Animals that can be used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses a mammalian ACTH-R, or any cell or cell line that expresses a mammalian ACTH-R or any epitope therein as a result of molecular or genetic engineering, or that has been treated to increase the expression of a mammalian ACTH-R by physical, biochemical or genetic means. Preferred cells are human cells, most preferably human 293 cells that have been transformed with a recombinant expression construct comprising DNA sequences encoding a mammalian ACTH-R and that express the mammalian ACTH-R gene product.

The present invention provides monoclonal antibodies that are immunologically reactive with an epitope that is a mammalian ACTH-R present on the surface of mammalian cells, preferably human or human cells. These antibodies are made using methods and techniques well known to those of skill in the art.

Monoclonal antibodies provided by the present invention are produced by hybridoma cell lines, that are also provided by the invention and that are made by methods well known in the art. Hybridoma cell lines are made by fusing individual cells of a myeloma cell line with spleen cells derived from animals immunized with cells expressing a mammalian ACTH-R, including human cells, as described above. The myeloma cell lines used in the invention include lines derived from myelomas of mice, rats, hamsters, primates and humans. Preferred mycloma cell line are from bovine, and the most preferred humans myeloma cell line is P3X63-Ag8.653. The animals from whom spleens are obtained after immunization are rats, mice and hamsters, preferably mice, most preferably Balb/c mice. Spleen cells and mycloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the perinal cavity of an animal, most preferably a mouse, and the monoclonal antibodies obtained from blood and/or ascites fluid.

Monoclonal antibodies provided by the present invention can also be produced by recombinant genetic methods well known to those of skill in the art, and the present invention encompasses antibodies made by such methods that are immunologically reactive with an epitope of a mammalian ACTH-R.

The present invention encompasses fragments of the antibody that are immunologically reactive with an epitope of a mammalian ACTH-R. Such fragments can be produced by any number of methods, including but not limited to proteolytic cleavage, chemical synthesis or preparation of such fragments by means of genetic engineering technology. The present invention also encompasses single-chain antibodies that are immunologically reactive with an epitope of a mammalian ACTH-R made by methods known to those of skill in the art The present invention also encompasses an epitope of a mammalian ACTH-R that is comprised of sequences and/or a conformation of sequences present in the mammalian ACTH-R molecule. This epitope may be naturally occurring, or may be the result of proteolytic cleavage of the mammalian ACTH-R molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of immunologically reactive light chain and heavy chain peptides to an epitope that is a mammalian ACTH-R. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They are set forth for explanatory purposes only, and are not to be ten as limiting the invention.

EXAMPLE 1

Isolation of an ACTH Receptor Probe by Random PCR Amplification of Human Melanoma cDNA Using Degenerate Oligonucleotide Primers In order to clone novel G-protein coupled receptors, human melanoma cDNA was used as template for a polymerase chain reaction (PCR)-based random cloning experiment. PCR was performed using a pair of degenerate oligonucleotide primers corresponding to the putative third and sixth transmembrane regions of G-protein coupled receptors (Libert et al., 1989, Science 244: 569–72; Zhou et al., 1990, Nature 347: 76–80). The PCR products obtained in this experiment were characterized by nucleotide sequencing. Two novel sequences representing novel G-protein-coupled receptors were identified.

PCR amplification was performed as follows. Total RNA was isolated from a human melanoma tumor sample by the guanidinium thiocyanate method (Chirgwin et al., 1979, Biochemistry 18: 5294–5299). Double-stranded cDNA was synthesized from total RNA with murine reverse transcriptase BRL, Gaithersburg, Md. by oligo-dT priming [Maniatis et al., *Molecular Cloning: A Laboratory Manual*, (Cold Spring Harbor Laboratory Press, Cold Spring Harbor, N.Y.), 1990]. The melanoma cDNA mixture was then subjected to 45 cycles of PCR amplification using 500 picomoles of degenerate oligonucleotide primers having the following sequence:

```
Primer III (sense):
    GAGTCGACCTGTG(CT)G(C/T)(C/G)AT(C/T)(A/G)CIIT(G/T)GAC(C/A)G(C/G)TAC
                              (SEQ ID NO:1)

and

Primer VI (antisense):
         CAGAATTCAG(T/A)AGGGCAICCAGCAGAI(G/C)(G/A)(T/C)GAA
                              (SEQ ID NO:2)
``` in 100 μl of a solution containing 50 mM Tris-HCl (pH 8.3), 2.5 mM MgCl$_2$, 0.01% gelatin, 200 μM each dNTP, and 2.5 units of Taq polymerase (Saiki et al., 1988, Science 239: 487–491). These primers were commercially synthesized by Research Genetics Ic. (Huntsville, Ala.). Each PCR amplification cycle consisted of incubations at 94° C. for 1 min (denaturation), 45° C. for 2 min (annealing), and 72° C. for 2 min (extension).

Amplified products of the PCR reaction were extracted with phenol/chloroform and precipitated with ethanol. After digestion with EcoRI and SalI, the PCR products were separated on a 1.2% agarose gel. A slice of this gel, corresponding to PCR products of 300 basepairs (bp) in size, was cut out and purified using glass beads and sodium iodide, and then the insert was cloned into a pBKS cloning vector (Stratagene, Laolla, Calif.).

A total of 172 of such pBKS clones containing inserts were sequenced using Sequenase (U.S. Biochemical Corp., Cleveland, Ohio) by the dideoxynucleotide chain termination mew (Sanger et al., 1977, Proc. Nad. Acad. Sci. USA 74: 5463–5467). Two typM of sequences homologous to other G-protein coupled receptors were identified.

EXAMPLE 2

Isolation and Characterization of Human ACTH-R Genomic Clones

In order to isolate the human gene corresponding to one of the two G-protein coupled receptor probes of Example 1, a human genomic library was screened at high stringency (50% formamide, 1M NaCl, 50 nM Tris-HCl, pH 7.5, 0.1% sodium pyrophosphate, 0.2% sodium dodecyl sulfate, 100 µg/ml salmon sperm DNA, 10× Denhardt's solution, 42° C.), using the human PCR fragments isolated as described in Example 1. Two different types of sequences were isolated, corresponding to the two PCR fragments, and were found to encode highly related G protein coupled rectors. These genomic clones were sequenced as described in Example 1. The nucleotide sequence of this clone is shown in FIGS. 1A–1C (SEQ ID NO:3). Nucleotide sequence analysis and homology comparisons were done on the OHSU computer system with software provided by Intelligenetics Inc. (Mountain View, Calif.).

One of these genomic clones was determine to encode an human MSH or (see copending U.S. patent application Ser. No. 07/866,979 now U.S. Pat. No. 5,532,347, issued Jul. 2, 1996). The human MSH receptor has a predicted amino acid sequence that is 75% identical and colinear with a mouse αMSH receptor cDNA sequence.

The second human genomic clone isolad encodes a highly related G-coupled receptor protein (SEQ ID NO:3). The predicted amino acid sequence (SEQ ID NO:4) of this clone (FIGS. 3A–3B, represented as human ACTH-R) is 39% identical and also colinear, excluding the third intracellular loop and carboxy-terminal tail, with the human MSH receptor gene product (FIGS. 3A–3B represented as human MSH-R). The predicted molecular weight of this putative ACTH-R is 33.9 kilodaltons (kD). Based on its high degree of homology to the murine (mouse MSH-R; FIGS. 3A–3B) and human MSH receptors, and the pattern of expression in different tissue types, as described in Example 3 below, this gene is a believed to encode a human ACTH receptor.

A bovine genomic DNA clone was isolated from a bovine genomic library, essentally as described above, and its nucleotide sequence determined (FIG. 2; SEQ ID NO: 5).

The predicted amino acid sequences of the mouse αMSH-R, human MSH-R, and the putative human ACTH-R are aligned in FIG. 3A through 3B. These sequences define the melanocortin receptors as a novel subfamily of the G protein-coupled receptors with a number of unusual features. The melanocortin receptors are the smallest G protein-coupled receptors identified to date (297–317aa) resulting from a short amino terminal extracellular domain, a short carboxy-terminal intracellular domain, and a very small third intracellular loop. The melanocortin receptors are lack several amino acid residues present in most G protein coupled receptors (see Probst et al., 1992, DNA & Cell Biol. 11: 1–20), including the proline residues in the 4th and 5th transmembrane domains, likely to introduce a bend in the alpha helical structure of the transmembrane domains and thought to be involved in the formation of the binding pocket (see Applebury & Hargrave, 1986, Vision Res. 26: 1881–1895), and one or both of the cysteine residues thought to form a disulfide bond between the first and second extracellular loops (see Dixon et al., 1987, EMBO J. 6: 3269–3275 and Karnik et al., 1988, Proc. Natl. Acad. Sci. USA 85: 8459–8463). Remarkably, the melanocortin receptors do not appear highly related to the other G protein-uplod receptors which recognize peptide ligands, such as the rectors for bombesin (see Spindel et at., 1990, Mol. Endocrinol. 4: 1956–1963) or substance K (see Masu et al., 1987, Nature 329: 836–838), but rather, are more closely related to the receptor for $\Delta^9$-tetradhydrocannabinol (see Matsuda et al., 1990, Nature 346: 561–564). For example, the human ACTH-R and rat cannabinoid receptors are about 30% identical in predicted transmembrane and intracellular loop amino acid sequences. The cannabinoid receptor also lacks the conserved proline in transmembrane 5 and the cysteine in the first extracellular loop necessary for disulfide bond formation. Least parsimony analysis with the receptor sequences shown in FIGS. 3A through 3B suggests the cannabinoid and melanocortin receptors may be evolutionarily related and form a subfamily distinct from the peptide receptors and the amine receptors. Regardless of whether the similarities are the result of evolutionary conservation or convergence, the sequence and putative structural similarities between the melanocortin and cannabinoid receptors may be informative in the search for the endogenous cannabinoid-like ligand.

EXAMPLE 3

Tissue Distribution of ACTH Receptor Gene Expression

To further gain insight into this receptor, we have examined the tissue distribution of its corresponding mRNA from various tissues by performing Northern hybridization experiments on RNA isolated from various tissues (see Maniatis et al., ibid.). The results of these experiments are shown in FIG. 4.

A panel of tissue samples was examined by Northern hybridization analysis performed under high stringency conditions. The nitrocellulose filter was hybridized with a putative human ACTH receptor probe to determine the distribution of receptor mRNA. In two primary human melanocyte cultures examined, the MSH-R is encoded by two mRNA species of approximately equal stoichiometry, one at 3.0 kb, and one which emigrates with murine αMSH-R mRNA at 3.9 kb.

Figure 5:
FIG. 5 illustrates localization of the putative ACTH receptor mRNA to the adrenal cortex by in situ hybridization (brightfield illumination).
Figure 6:
FIG. 6 illustrates location of the putative ACTH receptor mRNA to the adrenal cortex by in situ hybridization (darkfield illumination).

The putative human ACRH receptor is encoded predominantly by a single mRNA species of approximately 4.0 kb in the human adrenal gland, although several minor species are present as well. Northern analysis of a panel of tissues from the rhesus macaque performed under high stringency conditions demonstrate the existence of a cross-reacting 4.0 kb species specific to the rhesus adrenal gland (FIG. 4). In situ hybridization of a fragment of the putative human ACTH receptor to sections of rhesus adrenal tissue localized the expression of this receptor solely to the cortex, with no apparent hybridization to the medulla or capsule, as would be predicted for this receptor (FIGS. 5 & 6). Adrenal tissue from a juvenile rhesus macaque was fixed for 24 hours in 10% formalin in phosphate buffered saline, then incubated for 24 hours in 20% sucrose in PBS. Sections were prepared and hybridized with a 600 nucleotide $^{35}$S-labelled RNA antisense probe complementary to coding sequence spanning transmembrane domains 1–6 of the putative human ACTH receptor. Hybridizations were performed at 65° C. in 2×SSC and washed at 65° C. with 0.1×SSC.

The results of these experiments are shown in FIGS. 5 & 6. FIG. 5 illustrates lightfield micrograph of an hematoxylin and eosin stained section of rhesus adrenal showing capsule (C), zona glomerulosa (G), zona fasciculata (F), zona reticulata (R), and medulla (M). FIG. 6 depicts darkfield micrograph of the same field. Within the cortex, receptor expression was found across the entire *zona fascicutcua*, the site of glucocorticoid production, and in the cortical half of the *zona glomenrlosa*, the site of aldosterone synthesis. The *zona reficulata* was largely negative, except for a small band of hybridization adjacent to the medulla, which might result from a cross-reaction between the putative ACTH-R probe and a receptor for $_{γ3}$MSH, which is known to bind to this region of the adrenal cortex.

Additionally, we have been unable to detect expression in the brain of ACTH receptor described here, despite extensive documentation of ACTH binding sites there as well as in other tissues. These finding suggest the existence of alternate forms of these or related receptors that may be specifically expressed in brain tissue.

It should be understood that the foregoing disclosure emphasizes certain specific embodiments of the invention and that all modifications or alternatives equivalent thereto are within the spirit and scope of the invention as set forth in the appended claims.

We claim:

1. A method of screening a compound for binding to a mammalian adrenocorticotropic hormone receptor in cells expressing the a mammalian adrenocorticotropic hormone receptor, the method comprising the following steps:
   (a) transforming a host cell with a recombinant expression construct comprising a nucleic acid encoding mammalian adrenocorticotropic hormone receptor, wherein the nucleic acid encodes an amino acid sequence identified by Seq. I.D. Nos. 4 or 6 of, wherein the cells of the transformed cell culture express the receptor; and
   (b) assaying the transformed cell with the compound to determine whether the compound binds to the adrenocorticotropic hormone receptor.

2. The method of claim 1, wherein the mammalian adrenocorticotropic hormone receptor is a bovine adrenocorticotropic hormone receptor having an amino acid sequence identified as SEQ ID No. 4.

3. The method of claim 1, wherein the mammalian adrenocorticotropic hormone receptor is a human adrenocorticotropic hormone receptor having an amino acid sequence identified as SEQ ID No. 6.

4. A method of screening a compound for competitive binding to a mammalian adrenocorticotropic hormone receptor in cells expressing the mammalian adrenocorticotropic hormone receptor, the method comprising the following steps:
   (a) transforming a host cell with a recombinant expression construct encoding a mammalian adrenocorticotropic hormone recombinant expression construct comprising a nucleic acid encoding a mammalian adrenocorticotropic hormone receptor, wherein the nucleic acid encodes an amino acid sequence identified by Seq. I.D. Nos. 4 or 6, wherein the cells of the transformed cell culture express the receptor; and (b) assaying the transformed cell with the compound in the presence and in the absence of an agonist for the adrenocorticotropic hormone receptor; and (c) determining whether the compound competes with the agonist for binding to the adrenocorticotropic hormone receptor.

5. The method of claim 4, wherein the mammalian adrenocorticotropic hormone receptor is a bovine adrenocorticotropic hormone receptor having an amino acid sequence identified as SEQ ID No. 4.

6. The method of claim 4, wherein the mammalian adrenocorticotropic hormone receptor is a human adrenocorticotropic hormone receptor having an amino acid sequence identified as SEQ ID No. 6.

7. A method of screening a compound for binding to a mammalian adrenocorticotropic hormone receptor, the method comprising the following steps:

(a) transforming a eukaryotic cell culture with an expression construct comprising a nucleotide sequence encoding a mammalian adrenocorticotropic hormone receptor, wherein the nucleic acid encodes an amino acid sequence identified by Seq. I.D. Nos. 4 or 6, said construct being capable of expressing the adrenocorticotropic hormone receptor in a eukaryotic cell;

(b) obtaining a membrane preparation from the transformed cells;

(c) contacting the membrane preparations with an amount of the compound; and (d) assaying for the amount of the compound that binds to the adrenocorticotropic hormone receptor.

8. The method of claim 7 wherein the mammalian adrenocorticotropic hormone receptor is the bovine adrenocorticotropic hormone receptor having an amino acid sequence identified as SEQ ID No. 4.

9. The method of claim 7 wherein the mammalian adrenocorticotropic hormone receptor is the human adrenocorticotropic hormone receptor having an amino acid sequence identified as SEQ ID No. 6.

10. A method of performing a competitive binding assaying of a compound for assaying binding of the compound to a mammalian adrenocorticotropic hormone receptor, the method comprising the following steps:

(a) transforming a eukaryotic cell culture with an expression construct comprising a nucleotide sequence encoding a mammalian adrenocorticotropic hormone receptor, wherein the nucleic acid encodes an amino acid sequence identified by Seq. I.D. Nos. 4 or 6, said construct being capable of expressing the adrenocorticotropic hormone receptor in a eukaryotic cell;

(b) obtaining a membrane preparation from the transformed cells;

(c) contacting the membrane preparation with a detectably-labeled adrenocorticotropic hormone receptor agonist or antagonist in the presence of the compound; and (d) assaying for binding of the compound to the adrenocorticotropic hormone receptor by comparing the amount of the adrenocorticotropic hormone receptor agonist or antagonist that binds in the presence and absence of the compound.

11. The method of claim 10, wherein the mammalian adrenocorticotropic hormone receptor is the bovine adrenocorticotropic hormone receptor having an amino acid sequence identified as SEQ ID No. 4.

12. The method of claim 10 wherein the mammalian adrenocorticotropic hormone receptor is the human adrenocorticotropic hormone receptor having an amino acid sequence identified as SEQ ID No. 6.

13. A method for screening a compound for binding to a mammalian adrenocorticotropic hormone receptor wherein the compound is assayed for binding to a mammalian adrenocorticotropic hormone receptor using a cell membrane preparation comprising a adrenocorticotropic hormone receptor having an amino acid sequence identified by SEQ ID No.:4 or SEQ ID No.6, produced by a cell that expresses a recombinant expression vector encoding the adrenocorticotropic hormone receptor.

14. A method of screening a compound for competitive binding to a mammalian adrenocorticotropic hormone receptor, wherein the compound is assayed in the presence or absence of a detectable adrenocorticotropic hormone receptor agonist or antagonist for binding to a mammalian adrenocorticotropic hormone receptor using a cell membrane preparation comprising adrenocorticotropic hormone receptor having an amino acid sequence identified by SEQ ID No.:4 or SEQ ID No.6, produced by a cell that expresses a recombinant expression vector encoding the adrenocorticotropic hormone receptor.

* * * * *

```
                          SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1..33
         (D) OTHER INFORMATION: /function= "Degenerate
             oligonucleotide primer (sense)"

(xi) SEQUENCE DESCRIPTION: SEQ ID NO:1:

GAGTCGACCT GTGYGYSATY RCTKGACMGS TAC                               33

(2) INFORMATION FOR SEQ ID NO:2:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: YES (ix) FEATURE:
         (A) NAME/KEY: misc_feature
         (B) LOCATION: 1..31
         (D) OTHER INFORMATION: /function= "Degenerate
             oligonucleotide primer (antisense)"

(xi) SEQUENCE DESCRIPTION: SEQ ID NO:2:

CAGAATTCAG WAGGGCACCA GCAGASRYGA A                                 31

(2) INFORMATION FOR SEQ ID NO:3:

(i) SEQUENCE CHARACTERISTICS:
         (A) LENGTH: 2012 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: 694..1587
```

(D) OTHER INFORMATION: /product= "Human
            adrenocorticotropic hormone receptor"

(ix) FEATURE:
        (A) NAME/KEY: 5'UTR
        (B) LOCATION: 1..693

(ix) FEATURE:
        (A) NAME/KEY: 3'UTR
        (B) LOCATION: 1588..2012

(xi) SEQUENCE DESCRIPTION: SEQ ID NO:3:

```
ACAACACTTT ATATATATTT TTATAAATGT AAGGGGTACA AAGGTGCCAT TTTGTTACAT      60

GGATATACCG TGTAGTGGTG AAGCCTGGGC TTTTAGTGTA TCTGTCATCA GAATAACATA     120

CGTGTTACCC ATAGGAATTT CTCATCACCC GCCCCCTCCA CCCTTCGAGT CTCCAATGTC     180

CATTCCACAC TCTATATCCA CGTGTATGCA TATAGCTCCA CATATAAGTG AGAACATGTA     240

GTATTTGACT TCCTCTTTCT GAGTTATTTC ACTTTGATAA TGGCCTCCAC TTCCATCCAT     300

GTTGCTGCAA AAGACATGAC CTTATTCTTT TTGATAGCTG GGGAGTACTC CATTGTGTAT     360

ATGTACCACA TTTCTTTATC CATTCACCCA TTGAGAACAC TTAGTTGATT CCATATCTTT     420

GCTATTGTCA CTAGTGCTGC AATAAACATA CATGTGCAGG CTCCTTCTAA TATACTGATT     480

TATATTTTAT GGAGAGAGAT AGAGTTCTTA GCGAGTGTGC TGTTTATTTC TAGTGTACTT     540

GCAACTAATA TTCTGTATAC TCCCTTTAGG TGATTGGAGA TTTAACTTAG ATCTCCAGCA     600

AGTGCTACAA GAAGAAAAGA TCCTGAAGAA TCAATCAAGT TTCCGTGAAG TCAAGTCCAA     660

GTAACATCCC CGCCTTAACC ACAAGCAGGA GAA ATG AAG CAC ATT ATC AAC TCG     714
                                     Met Lys His Ile Ile Asn Ser
                                       1               5

TAT GAA AAC ATC AAC AAC ACA GCA AGA AAT AAT TCC GAC TGT CCT CGT      762
Tyr Glu Asn Ile Asn Asn Thr Ala Arg Asn Asn Ser Asp Cys Pro Arg
        10                  15                  20

GTG GTT TTG CCG GAG GAG ATA TTT TTC ACA ATT TCC ATT GTT GGA GTT      810
Val Val Leu Pro Glu Glu Ile Phe Phe Thr Ile Ser Ile Val Gly Val
            25                  30                  35

TTG GAG AAT CTG ATC GTC CTG CTG GCT GTG TTC AAG AAT AAG AAT CTC      858
Leu Glu Asn Leu Ile Val Leu Leu Ala Val Phe Lys Asn Lys Asn Leu
 40                  45                  50                  55

CAG GCA CCC ATG TAC TTT TTC ATC TGT AGC TTG GCC ATA TCT GAT ATG      906
Gln Ala Pro Met Tyr Phe Phe Ile Cys Ser Leu Ala Ile Ser Asp Met
                60                  65                  70

CTG GGC AGC CTA TAT AAG ATC TTG GAA AAT ATC CTG ATC ATA TTG AGA      954
Leu Gly Ser Leu Tyr Lys Ile Leu Glu Asn Ile Leu Ile Ile Leu Arg
            75                  80                  85

AAC ATG GGC TAT CTC AAG CCA CGT GGC AGT TTT GAA ACC ACA GCC GAT     1002
Asn Met Gly Tyr Leu Lys Pro Arg Gly Ser Phe Glu Thr Thr Ala Asp
        90                  95                 100

GAC ATC ATC GAC TCC CTG TTT GTC CTC TCC CTG CTT GGC TCC ATC TTC     1050
Asp Ile Ile Asp Ser Leu Phe Val Leu Ser Leu Leu Gly Ser Ile Phe
    105                 110                 115

AGC CTG TCT GTG ATT GCT GCG GAC CGC TAC ATC ACC ATC TTC CAC GCA     1098
Ser Leu Ser Val Ile Ala Ala Asp Arg Tyr Ile Thr Ile Phe His Ala
120                 125                 130                 135

CTG CGG TAC CAC AGC ATC GTG ACC ATG CGC CGC ACT GTG GTG GTG CTT     1146
Leu Arg Tyr His Ser Ile Val Thr Met Arg Arg Thr Val Val Val Leu
                140                 145                 150

ACG GTC ATC TGG ACG TTC TGC ACG GGG ACT GGC ATC ACC ATG GTG ATC     1194
Thr Val Ile Trp Thr Phe Cys Thr Gly Thr Gly Ile Thr Met Val Ile
            155                 160                 165
```

```
TTC TCC CAT CAT GTG CCC ACA GTG ATC ACC TTC ACG TCG CTG TTC CCG      1242
Phe Ser His His Val Pro Thr Val Ile Thr Phe Thr Ser Leu Phe Pro
            170                 175                 180

CTG ATG CTG GTC TTC ATC CTG TGC CTC TAT GTG CAC ATG TTC CTG CTG      1290
Leu Met Leu Val Phe Ile Leu Cys Leu Tyr Val His Met Phe Leu Leu
        185                 190                 195

GCT CGA TCC CAC ACC AGG AAG ATC TCC ACC CTC CCC AGA GCC AAC ATG      1338
Ala Arg Ser His Thr Arg Lys Ile Ser Thr Leu Pro Arg Ala Asn Met
200                 205                 210                 215

AAA GGG GCC ATC ACA CTG ACC ATC CTG CTC GGG GTC TTC ATC TTC TGC      1386
Lys Gly Ala Ile Thr Leu Thr Ile Leu Leu Gly Val Phe Ile Phe Cys
            220                 225                 230

TGG GCC CCC TTT GTG CTT CAT GTC CTC TTG ATG ACA TTC TGC CCA AGT      1434
Trp Ala Pro Phe Val Leu His Val Leu Leu Met Thr Phe Cys Pro Ser
        235                 240                 245

AAC CCC TAC TGC GCC TGC TAC ATG TCT CTC TTC CAG GTG AAC GGC ATG      1482
Asn Pro Tyr Cys Ala Cys Tyr Met Ser Leu Phe Gln Val Asn Gly Met
            250                 255                 260

TTG ATC ATG TGC AAT GCC GTC ATT GAC CCC TTC ATA TAT GCC TTC CGG      1530
Leu Ile Met Cys Asn Ala Val Ile Asp Pro Phe Ile Tyr Ala Phe Arg
        265                 270                 275

AGC CCA GAG CTC AGG GAC GCA TTC AAA AAG ATG ATC TTC TGC AGC AGG      1578
Ser Pro Glu Leu Arg Asp Ala Phe Lys Lys Met Ile Phe Cys Ser Arg
280                 285                 290                 295

TAC TGG TAGAATGGCT GATCCCTGGT TTTAGAATCC ATGGGAATAA CGTTGCCAAG       1634
Tyr Trp

TGCCAGAATA GTGTAACATT CCAACAAATG CCAGTGCTCC TCACTGGCCT TCCTTCCCTA    1694

ATGGATGCAA GGATGACCCA CCAGCTAGTG TTTCTGAATA CTATGGCCAG GAACAGTCTA    1754

TTGTAGGGGC AACTCTATTT GTGACTGGAC AGATAAAACG TGTAGTAAAA GAAGGATAGA    1814

ATACAAAGTA TTAGGTACAA AAGTAATTAG GTTTGCATTA CTTATGACAA ATGCATTACT    1874

TTTGCACCAA TCTAGTAAAA CAGCAATAAA AATTCAAGGG CTTTGGGCTA AGGCAAAGAC    1934

TTGCTTTCCT GTGGACATTA ACAAGCCAGT TCTGAGGCGG CCTTTCCAGG TGGAGGCCAT    1994

TGCAGCCAAT TTCAGAGT                                                  2012

(2) INFORMATION FOR SEQ ID NO:4:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO:4:

Met Lys His Ile Ile Asn Ser Tyr Glu Asn Ile Asn Asn Thr Ala Arg
  1               5                  10                  15

Asn Asn Ser Asp Cys Pro Arg Val Val Leu Pro Glu Glu Ile Phe Phe
                20                  25                  30

Thr Ile Ser Ile Val Gly Val Leu Glu Asn Leu Ile Val Leu Leu Ala
            35                  40                  45

Val Phe Lys Asn Lys Asn Leu Gln Ala Pro Met Tyr Phe Phe Ile Cys
        50                  55                  60

Ser Leu Ala Ile Ser Asp Met Leu Gly Ser Leu Tyr Lys Ile Leu Glu
65                  70                  75                  80

Asn Ile Leu Ile Ile Leu Arg Asn Met Gly Tyr Leu Lys Pro Arg Gly
                85                  90                  95
```

```
Ser Phe Glu Thr Thr Ala Asp Asp Ile Ile Asp Ser Leu Phe Val Leu
            100                 105                 110

Ser Leu Leu Gly Ser Ile Phe Ser Leu Ser Val Ile Ala Ala Asp Arg
        115                 120                 125

Tyr Ile Thr Ile Phe His Ala Leu Arg Tyr His Ser Ile Val Thr Met
    130                 135                 140

Arg Arg Thr Val Val Val Leu Thr Val Ile Trp Thr Phe Cys Thr Gly
145                 150                 155                 160

Thr Gly Ile Thr Met Val Ile Phe Ser His His Val Pro Thr Val Ile
                165                 170                 175

Thr Phe Thr Ser Leu Phe Pro Leu Met Leu Val Phe Ile Leu Cys Leu
            180                 185                 190

Tyr Val His Met Phe Leu Leu Ala Arg Ser His Thr Arg Lys Ile Ser
        195                 200                 205

Thr Leu Pro Arg Ala Asn Met Lys Gly Ala Ile Thr Leu Thr Ile Leu
    210                 215                 220

Leu Gly Val Phe Ile Phe Cys Trp Ala Pro Phe Val Leu His Val Leu
225                 230                 235                 240

Leu Met Thr Phe Cys Pro Ser Asn Pro Tyr Cys Ala Cys Tyr Met Ser
                245                 250                 255

Leu Phe Gln Val Asn Gly Met Leu Ile Met Cys Asn Ala Val Ile Asp
            260                 265                 270

Pro Phe Ile Tyr Ala Phe Arg Ser Pro Glu Leu Arg Asp Ala Phe Lys
        275                 280                 285

Lys Met Ile Phe Cys Ser Arg Tyr Trp
290                 295

(2) INFORMATION FOR SEQ ID NO:5:

(i) SEQUENCE CHARACTERISTICS:
        (A) LENGTH: 1108 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 133..1026

(ix) FEATURE:
        (A) NAME/KEY: 5'UTR
        (B) LOCATION: 1..132

(ix) FEATURE:
        (A) NAME/KEY: 3'UTR
        (B) LOCATION: 1027..1106

(xi) SEQUENCE DESCRIPTION: SEQ ID NO:5:

GGGGCCAGAA AGTTCCTGCT TCAGAGCAGA AGATCTTCAG CAAGAACTAC AAAGAAGAAA        60

AGATTCTGGA GAATCAATCA AGTTTCCTGT CAAGTTCCAG TAACGTTTCT GTCTTAACTG       120

CACACAGGAA AG ATG AAA CAC ATT CTC AAT CTG TAT GAA AAC ATC AAC           168
              Met Lys His Ile Leu Asn Leu Tyr Glu Asn Ile Asn
                1               5                   10

AGT ACA GCA AGA AAT AAC TCA GAC TGT CCT GCT GTG ATT TTG CCA GAA         216
Ser Thr Ala Arg Asn Asn Ser Asp Cys Pro Ala Val Ile Leu Pro Glu
            15                  20                  25

GAG ATA TTT TTC ACA GTA TCC ATT GTT GGG GTT TTG GAG AAC CTG ATG         264
Glu Ile Phe Phe Thr Val Ser Ile Val Gly Val Leu Glu Asn Leu Met
        30                  35                  40
```

```
GTC CTT CTG GCT GTG GCC AAG AAT AAG AGT CTT CAG TCG CCC ATG TAC        312
Val Leu Leu Ala Val Ala Lys Asn Lys Ser Leu Gln Ser Pro Met Tyr
 45                  50                  55                  60

TTT TTC ATC TGC AGC TTG GCT ATT TCC GAT ATG CTG GGG AGC CTG TAC        360
Phe Phe Ile Cys Ser Leu Ala Ile Ser Asp Met Leu Gly Ser Leu Tyr
                 65                  70                  75

AAG ATT TTG GAA AAC GTT CTG ATC ATG TTC AAA AAC ATG GGT TAC CTC        408
Lys Ile Leu Glu Asn Val Leu Ile Met Phe Lys Asn Met Gly Tyr Leu
             80                  85                  90

GAG CCT CGA GGC AGT TTT GAA AGC ACA GCA GAT GAT GTG GTG GAC TCC        456
Glu Pro Arg Gly Ser Phe Glu Ser Thr Ala Asp Asp Val Val Asp Ser
         95                 100                 105

CTG TTC ATC CTC TCC CTT CTC GGC TCC ATC TGC AGC CTG TCT GTG ATT        504
Leu Phe Ile Leu Ser Leu Leu Gly Ser Ile Cys Ser Leu Ser Val Ile
    110                 115                 120

GCC GCT GAC CGC TAC ATC ACA ATC TTC CAC GCT CTG CAG TAC CAC CGC        552
Ala Ala Asp Arg Tyr Ile Thr Ile Phe His Ala Leu Gln Tyr His Arg
125                 130                 135                 140

ATC ATG ACC CCC GCA CCG TGC CCT CGT CAT CTG ACG GTC CTC TGG GCA        600
Ile Met Thr Pro Ala Pro Cys Pro Arg His Leu Thr Val Leu Trp Ala
                145                 150                 155

GGC TGC ACA GGC AGT GGC ATT ACC ATC GTG ACC TTC TCC CAT CAC GTC        648
Gly Cys Thr Gly Ser Gly Ile Thr Ile Val Thr Phe Ser His His Val
            160                 165                 170

CCC ACA GTG ATC GCC TTC ACA GCG CTG TTC CCG CTG ATG CTG GCC TTC        696
Pro Thr Val Ile Ala Phe Thr Ala Leu Phe Pro Leu Met Leu Ala Phe
        175                 180                 185

ATC CTG TGC CTC TAC GTG CAC ATG TTC CTG CTG GCC CGC TCC CAC ACC        744
Ile Leu Cys Leu Tyr Val His Met Phe Leu Leu Ala Arg Ser His Thr
    190                 195                 200

AGG AGG ACC CCC TCC CTT CCC AAA GCC AAC ATG AGA GGG GCC GTC ACA        792
Arg Arg Thr Pro Ser Leu Pro Lys Ala Asn Met Arg Gly Ala Val Thr
205                 210                 215                 220

CTG ACT GTC CTG CTC GGG GTC TTC ATT TTC TGT TGG GCA CCC TTT GTC        840
Leu Thr Val Leu Leu Gly Val Phe Ile Phe Cys Trp Ala Pro Phe Val
                225                 230                 235

CTT CAT GTC CTC TTG ATG ACA TTC TGC CCA GCT GAC CCC TAC TGT GCC        888
Leu His Val Leu Leu Met Thr Phe Cys Pro Ala Asp Pro Tyr Cys Ala
            240                 245                 250

TGC TAC ATG TCC CTC TTC CAG GTG AAT GGT GTG TTG ATC ATG TGT AAT        936
Cys Tyr Met Ser Leu Phe Gln Val Asn Gly Val Leu Ile Met Cys Asn
        255                 260                 265

GCC ATC ATC GAC CCC TTC ATA TAT GCC TTT CGG AGC CCA GAG CTC AGG        984
Ala Ile Ile Asp Pro Phe Ile Tyr Ala Phe Arg Ser Pro Glu Leu Arg
    270                 275                 280

GTC GCA TTC AAA AAG ATG GTT ATC TGC AAC TGT TAC CAG TAGAATGATT        1033
Val Ala Phe Lys Lys Met Val Ile Cys Asn Cys Tyr Gln
285                 290                 295

GGTCCCTGAT TTAGGAGCC ACAGGGATAT ACTGTCAGGG ACAGAGTAGC GTGACAGACC      1093

AACAACACTA GGACT                                                      1108

(2) INFORMATION FOR SEQ ID NO:6:

(i) SEQUENCE CHARACTERISTICS:
        (A) LENGTH: 297 amino acids
        (B) TYPE: amino acid
        (D) TOPOLOGY: linear (ii) MOLECULE TYPE: protein
```

-continued (xi) SEQUENCE DESCRIPTION: SEQ ID NO:6:

```
Met Lys His Ile Leu Asn Leu Tyr Glu Asn Ile Asn Ser Thr Ala Arg
 1               5                  10                  15

Asn Asn Ser Asp Cys Pro Ala Val Ile Leu Pro Glu Glu Ile Phe Phe
            20                  25                  30

Thr Val Ser Ile Val Gly Val Leu Glu Asn Leu Met Val Leu Leu Ala
            35                  40                  45

Val Ala Lys Asn Lys Ser Leu Gln Ser Pro Met Tyr Phe Phe Ile Cys
 50                  55                  60

Ser Leu Ala Ile Ser Asp Met Leu Gly Ser Leu Tyr Lys Ile Leu Glu
 65                  70                  75                  80

Asn Val Leu Ile Met Phe Lys Asn Met Gly Tyr Leu Glu Pro Arg Gly
                85                  90                  95

Ser Phe Glu Ser Thr Ala Asp Asp Val Val Asp Ser Leu Phe Ile Leu
            100                 105                 110

Ser Leu Leu Gly Ser Ile Cys Ser Leu Ser Val Ile Ala Ala Asp Arg
            115                 120                 125

Tyr Ile Thr Ile Phe His Ala Leu Gln Tyr His Arg Ile Met Thr Pro
130                 135                 140

Ala Pro Cys Pro Arg His Leu Thr Val Leu Trp Ala Gly Cys Thr Gly
145                 150                 155                 160

Ser Gly Ile Thr Ile Val Thr Phe Ser His His Val Pro Thr Val Ile
                165                 170                 175

Ala Phe Thr Ala Leu Phe Pro Leu Met Leu Ala Phe Ile Leu Cys Leu
                180                 185                 190

Tyr Val His Met Phe Leu Leu Ala Arg Ser His Thr Arg Arg Thr Pro
            195                 200                 205

Ser Leu Pro Lys Ala Asn Met Arg Gly Ala Val Thr Leu Thr Val Leu
    210                 215                 220

Leu Gly Val Phe Ile Phe Cys Trp Ala Pro Phe Val Leu His Val Leu
225                 230                 235                 240

Leu Met Thr Phe Cys Pro Ala Asp Pro Tyr Cys Ala Cys Tyr Met Ser
                245                 250                 255

Leu Phe Gln Val Asn Gly Val Leu Ile Met Cys Asn Ala Ile Ile Asp
            260                 265                 270

Pro Phe Ile Tyr Ala Phe Arg Ser Pro Glu Leu Arg Val Ala Phe Lys
            275                 280                 285

Lys Met Val Ile Cys Asn Cys Tyr Gln
            290                 295
```